United States Patent
Zhang et al.

(10) Patent No.: US 12,121,542 B2
(45) Date of Patent: *Oct. 22, 2024

(54) BCMA CHIMERIC ANTIGEN RECEPTOR BASED ON SINGLE DOMAIN ANTIBODY AND USE THEREOF

(71) Applicant: SHENZHEN PREGENE BIOPHARMA CO. LTD., Shenzhen (CN)

(72) Inventors: Jishuai Zhang, Shenzhen (CN); Hongjian Li, Shenzhen (CN); Hongchang Su, Shenzhen (CN); Chaolemeng Bao, Shenzhen (CN); Zongpei Song, Shenzhen (CN); Qinghua Cai, Shenzhen (CN); Yijin Ding, Shenzhen (CN); Zhibo Cai, Shenzhen (CN)

(73) Assignee: SHENZHEN PREGENE BIOPHARMA CO. LTD., Shenzhen (CN)

( * ) Notice: Subject to any disclaimer, the term of this patent is extended or adjusted under 35 U.S.C. 154(b) by 914 days.

This patent is subject to a terminal disclaimer.

(21) Appl. No.: 17/270,775

(22) PCT Filed: Jul. 10, 2019

(86) PCT No.: PCT/CN2019/095505
§ 371 (c)(1),
(2) Date: Feb. 23, 2021

(87) PCT Pub. No.: WO2020/038146
PCT Pub. Date: Feb. 27, 2020

(65) Prior Publication Data
US 2022/0218746 A1    Jul. 14, 2022

(30) Foreign Application Priority Data
Aug. 24, 2018   (CN) .......................... 201810972053.8

(51) Int. Cl.
| | | |
|---|---|---|
| *A61K 35/17* | (2015.01) | |
| *A61K 39/00* | (2006.01) | |
| *A61P 35/02* | (2006.01) | |
| *C07K 14/725* | (2006.01) | |
| *C07K 16/28* | (2006.01) | |

(52) U.S. Cl.
CPC .......... *A61K 35/17* (2013.01); *A61K 39/4611* (2023.05); *A61K 39/4631* (2023.05); *A61P 35/02* (2018.01); *C07K 14/7051* (2013.01); *C07K 16/2878* (2013.01); *C07K 2317/22* (2013.01); *C07K 2317/569* (2013.01)

(58) Field of Classification Search
CPC ................ A61K 35/17; A61K 39/4611; A61K 39/4631; A61K 39/464417; A61K 2239/46; A61P 35/02; A61P 35/00; C07K 14/7051; C07K 16/2878; C07K 2317/22; C07K 2317/569; C07K 2319/03; C07K 2317/565; C07K 2317/622; C07K 2319/00; C07K 2319/33; C07K 2319/74; C07K 2317/53; C12N 2510/00; C12N 5/0636; C12N 5/0646

See application file for complete search history.

(56) References Cited

U.S. PATENT DOCUMENTS

| | | | |
|---|---|---|---|
| 10,174,095 | B2 | 1/2019 | Brogdon et al. |
| 10,383,929 | B2 | 8/2019 | Morgan et al. |
| 2016/0046724 | A1 | 2/2016 | Brogdon et al. |
| 2017/0226216 | A1 | 8/2017 | Morgan et al. |
| 2018/0085444 | A1 | 3/2018 | Morgan et al. |
| 2018/0094280 | A1 | 4/2018 | Kutner et al. |
| 2018/0230225 | A1 | 8/2018 | Fan et al. |
| 2019/0153061 | A1 | 5/2019 | Brogdon et al. |
| 2021/0163615 | A1* | 6/2021 | Fan .................. C12N 5/10 |

FOREIGN PATENT DOCUMENTS

| | | |
|---|---|---|
| CN | 105777911 A | 7/2016 |
| CN | 106687483 A | 5/2017 |
| CN | 106795217 A | 5/2017 |
| CN | 107207598 A | 9/2017 |
| CN | 107614008 A | 1/2018 |
| WO | WO 2017/130223 A2 | 8/2017 |

OTHER PUBLICATIONS

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. doi: 10.4049/jimmunol.165.8.4505. PMID: 11035090. (Year: 2000).*

Teng S, Srivastava AK, Schwartz CE, Alexov E, Wang L. Structural assessment of the effects of amino acid substitutions on protein stability and protein protein interaction. Int J Comput Biol Drug Des. 2010;3(4):334-49. doi: 10.1504/IJCBDD.2010.038396. Epub Feb. 4, 2011. PMID: 21297231. (Year: 2010).*

Zhang C, Liu J, Zhong JF, Zhang X. Engineering CAR-T cells. Biomark Res. Jun. 24, 2017;5:22. doi: 10.1186/s40364-017-0102-y. PMID: 28652918; PMCID: PMC5482931. (Year: 2017).*

(Continued)

*Primary Examiner* — Hong Sang
*Assistant Examiner* — Carol Ann Chase
(74) *Attorney, Agent, or Firm* — Merchant & Gould, P.C.; Daniel J. Pereira

(57) ABSTRACT

A chimeric antigen receptor (CAR) may be include: a BCMA binding domain, a transmembrane domain, a costimulatory domain, and an intracellular signaling domain, wherein the BCMA binding domain includes heavy chain complementarity determining regions HCDR1-3, and the amino acid sequences of the HCDR1-3 are successively as shown in SEQ ID NO: 1-3.

18 Claims, 5 Drawing Sheets
Specification includes a Sequence Listing.

(56) References Cited

OTHER PUBLICATIONS

Leader Sequence—OxfordReference.com, accessed Mar. 9, 2024.*
Extended European Search Report issued on Apr. 7, 2022 in European Patent Application No. 19852889.5, 10 pages.
Anonymous, BCMA Nano Antibody CAR-T Cells for Patients With Refractory and Relapsed Multiple Myeloma (BCMA CAR-T), NIH U.S. National Library of Medicine, Sep. 7, 2018, Retrieved from the Internet: URL:https://clinicaltrials.gov/ct2/show/NCT03661554, 7 pages, XP055906446.
De Munter et al., "Nanobody Based Dual Specific CARs", International Journal of Molecular Sciences, 2018, vol. 19, pp. 1-11, XP055609787.
International Search Report issued on Oct. 9, 2019 in PCT/CN2019/095505 filed on Jul. 10, 2019, 5 pages.
Wu et al., "A Novel VHH Antibody Targeting the B Cell-Activating Factor for B-Cell Lymphoma", International Journal of Molecular Sciences, ISSN 1422-0067, 2014, vol. 15, pp. 9481-9496.
Tai et al., "Targeting B-cell maturation antigen in multiple myeloma", Immunotherapy, 2015, vol. 7, No. 11, pp. 1187-1199.
Eurasian Office Action issued Jan. 30, 2023 in Eurasian Patent Application No. 202190607 (with English language translation), 4 pages.
R. Coico, et al., "Immunology Manual," Publishing Center Academy, 2008, 3 pages.
E.P. Altshuler, et al., "Recombinant antibodies production and methods for increasing their affinity," Advances in Biological Chemistry, vol. 50, 2010, 2 pages.
Bu, D.-X., et al., "Pre-clinical validation of B cell maturation antigen (BCMA) as a target for T cell immunotherapy of multiple myeloma", Oncotarget, vol. 9, No. 40, pp. 25764-25780.

* cited by examiner

A  Killing Effects of BCMA CART on K562

B  Killing Effects of BCMA CART on MM.1S

BCMA CHIMERIC ANTIGEN RECEPTOR BASED ON SINGLE DOMAIN ANTIBODY AND USE THEREOF

CROSS REFERENCE TO RELATED APPLICATIONS

This application is a National Stage Application and claims priority under 35 U.S.C. § 371 to Patent Cooperation Treaty application PCT/CN2019/095505, filed Jul. 10, 2019 which claims the benefit of CN application CN201810972053.8, filed Aug. 24, 2018. Priority is claimed to these applications and the disclosure of each of these applications, to the extent allowed, is incorporated herein by reference.

SEQUENCE LISTING

The instant application contains a Sequence Listing which has been submitted electronically in ASCII format and is hereby incorporated by reference in its entirety. Said ASCII copy, created on Aug. 11, 2021, is named 535125USSL.txt and is 17,481 bytes in size.

TECHNICAL FIELD

The present application belongs to the field of immune cell therapy, in particular, to a BCMA chimeric antigen receptor based on a single domain antibody and use thereof.

BACKGROUND

Multiple myeloma (MM) is a hematologic tumor occurring in bone marrow, and characterized by accumulation of clonal plasma cells. The therapeutic regimen mainly focuses on the apoptosis of plasma cells, and/or the reduction of osteoclast activity (e.g., chemotherapy, thalidomide, lenalidomide, diphosphate, and/or proteasome inhibitor, such as, bortezomib (VELCADE®) or carfilzomib). Currently, multiple myeloma is still an intractable disease. Only about 45% of the patients can live over five years after diagnosis. Many patients will experience disease relapse after treatment suspension, and the 5-year survival rate of patients after relapse is less than 20%.

In recent years, chimeric antigen receptor T-cell immunotherapy (CART) has become one of the most promising tumor immunotherapies. Chimeric antigen receptor consists of one tumor-associated antigen binding domain, a transmembrane domain, a co-stimulatory domain, and an intracellular signaling domain. CART cell therapy generally expresses the fusion protein of the minimum antibody binding fragment for recognizing tumor-associated antigen (single chain fragment variable, or scFv) and T cell activation sequence on the surface of T cells by gene transduction technology. T cells expressing CAR molecules bind to tumor antigens in an antigen-dependent but non-MHC restricted manner to specifically kill tumor cells.

The effectiveness of CART cell therapy depends on properties like the specificity of antibodies recognizing the tumor-associated antigens, the affinity of antigen binding, or the like. Currently, the design of intracellular signaling domain of CART cells has become mature, and the design of antigen binding domain has become the focus and key of the development of novel CART technology. A minimum and single functional domain antibody fragment capable of completely binding to an antigen in an alpaca heavy chain antibody (HCAb), namely, a variable region of a heavy chain antibody which is free of light chain (also known as VHH), has a simple structure and a molecular weight of about ⅒ of that of a common antibody. It can be effectively expressed and purified in an in vitro expression system (e.g., E. coli, yeast, eukaryotic cells, and plants). It has high specificity, high affinity, low immunogenicity, good infiltration, and has a possibility of contacting relatively hidden targets which are unlikely to be contacted by conventional antibodies upon tumor treatment. Based on these advantages, it is one of the development tendencies of CART cell therapies to use single domain antibodies as antigen binding region of CAR to modify CAR.

For B-cell lineage malignancies, BCMA (B-cell maturation antigen) is a very important B-cell biomarker. Its RNA is almost always found in multiple myeloma cells, and the protein is also found on the surface of malignant plasma cells in patients with multiple myeloma. BCMA is a type III transmembrane protein composed of 185 amino acid residues, and belongs to TNF receptor superfamily, and its ligand belongs to TNF superfamily, such as, proliferation inducing ligand (APRIL) B lymphocyte stimulating factor (BAFF). BCMA can activate the proliferation and survival of B cells by binding to its ligands. BCMA is highly expressed on the surface of plasma cells and multiple myeloma cells, but not expressed in hematopoietic stem cells or other normal tissue cells. Therefore, BCMA can be used as an ideal target for targeted therapy of MM.

SUMMARY OF THE INVENTION

The present application designs a specific single domain antibody as an antigen binding region of CAR for use in CAR modifications and CART cell therapies by means of genetic engineering, and proposes a specific chimeric antigen receptor (CAR) based on a single domain antibody, which includes a target binding domain, a transmembrane domain, one or more co-stimulatory domains, and an intracellular signaling domain, wherein the extracellular domain is a fragment of antigen binding which can bind to human BCMA (B cell mature antigen).

In an aspect, the present application provides a chimeric antigen receptor (CAR), including: BCMA binding domain, a transmembrane domain, one or more co-stimulatory domains, and an intracellular signaling domain; wherein the BCMA binding domain includes a heavy chain complementary determining region 1 (HCDR1), a heavy chain complementary determining region 2 (HCDR2), and a heavy chain complementary determining region 3 (HCDR3), wherein the amino acid sequence of the HCDR1 is as set forth in SEQ ID NO: 1, the amino acid sequence of the HCDR2 is as set forth in SEQ ID NO: 2, and the amino acid sequence of the HCDR3 is as set forth in SEQ ID NO: 3.

In some embodiments, the BCMA binding domain is a single domain antibody.

In some embodiments, the BCMA binding domain includes an amino acid sequence as set forth in SEQ ID NO:4 or a functional variant thereof.

In some embodiments, the transmembrane domain includes a polypeptide derived from a protein selected from the group consisting of a, p, or (chain of a T-cell receptor, CD28, CD3e, CD45, CD4, CD5, CD8a, CD9, CD16, CD22, CD33, CD37, CD64, CD80, CD86, CD134, CD137, and CD154.

In some embodiments, the transmembrane domain comprises an amino acid sequence as set forth in SEQ ID NO:5 or a functional variant thereof.

In some embodiments, the BCMA binding domain is linked to the transmembrane domain via a hinge region.

In some embodiments, the hinge region comprises an amino acid sequence as set forth in SEQ ID NO:6 or a functional variant thereof.

In some embodiments, the one or more co-stimulatory domains are derived from a co-stimulatory molecule selected from the group consisting of CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKG2C, SLP76, TRIM, and ZAP70.

In some embodiments, the co-stimulatory domain comprises an amino acid sequence as set forth in SEQ ID NO:7 or a functional variant thereof.

In some embodiments, the intracellular signaling domain comprises a signaling domain of CD3ζ.

In some embodiments, the intracellular signaling domain comprises an amino acid sequence as set forth in SEQ ID NO:8 or a functional variant thereof.

In some embodiments, the CAR further comprises a leader sequence, and the leader sequence comprises an amino acid sequence as set forth in SEQ ID NO:9 or a functional variant thereof.

In some embodiments, the CAR comprises an amino acid sequence as set forth in SEQ ID NOs:10-11 or a functional variant thereof.

In another aspect, the present application provides an isolated nucleic acid molecule encoding the CAR.

In some embodiments, the nucleic acid molecule comprises a nucleic acid sequence as set forth in SEQ ID NOs:12-13 or a functional variant thereof.

In another aspect, the present application provides a vector comprising the nucleic acid molecule.

In some embodiments, the vector is selected from DNA vectors, RNA vectors, plasmids, lentiviral vectors, adenoviral vectors, and retroviral vectors.

In some embodiments, the vector further comprises an EF1 promoter, the EF1 promoter comprises a sequence as set forth in SEQ ID NO: 14.

In another aspect, the present application provides an immune effector cell comprising the CAR, the nucleic acid molecule, or the vector.

In some embodiments, the immune effector cell is selected from T lymphocytes and natural killer (NK) cells.

In another aspect, the present application provides a method of preparing an immune effector cell including introducing the vector into an immune effector cell.

In some embodiments, in the method, the immune effector cell is selected from T lymphocytes and natural killer (NK) cells.

In another aspect, the present application provides a composition including the immune effector cell.

In another aspect, the present application provides use of the CAR, the nucleic acid molecule, the vector, or the immune effector cell in manufacture of a drug for treating a disease or disorder associated with the expression of BCMA.

In another aspect, the present application provides the CAR, the nucleic acid molecule, the vector, or the immune effector cell for treating a disease or disorder associated with the expression of BCMA.

In another aspect, the present application provides a method of treating a disease or disorder associated with the expression of BCMA including the step of administering the CAR, the nucleic acid molecule, the vector, or the immune effector cell to a subject.

In some embodiments, the disease or disorder associated with the expression of BCMA is cancer or malignant tumor.

In some embodiments, the disease or disorder associated with the expression of BCMA is selected from the group consisting of B cell acute lymphoblastic leukemia, T cell acute lymphoblastic leukemia, acute lymphoblastic leukemia, chronic myeloid leukemia, chronic lymphocytic leukemia, B cell prolymphocytic leukemia, blast cell plasmacytoid dendritic cytoma, Burkitt's lymphoma, diffuse large B cell lymphoma, follicular lymphoma, hairy cell leukemia, small or large cell follicular lymphoma, malignant lymphoproliferative condition, MALT lymphoma, mantle cell lymphoma, marginal zone lymphoma, multiple myeloma, myelodysplasia, and myelodysplastic syndrome, non-Hodgkin lymphoma, plasmablast lymphoma, plasmacytoid dendritic cytoma, Waldenstrom macroglobulinemia, prostatic cancer, pancreatic cancer, lung cancer, myeloma, MGUS, plasmacytoma, systemic amyloid light chain amyloidosis, and POEMS syndrome.

Innovation and Beneficial Effects of the Present Application

The applicant has designed a single domain antibody comprising a specific amino acid sequence by means of genetic engineering, and constructed a chimeric antigen receptor (CAR) by using the single domain antibody as a binding domain (BCMA binding domain). It has been found through research that the immune cells (e.g., CART cells) comprising the chimeric antigen receptor have strong killing ability and specificity to related tumors. In particular, the CAR efficiently transduces healthy human T lymphocytes in vitro, and produces a strong killing effect on BCMA-positive target cells; and in the in vivo experiments, it also shows a strong killing effect: a mouse model bearing a primary myeloma is established for detection by using MM.1S cells transfected with luciferase, and after 3 days of administration, most of the fluorescence disappears, indicating that the CART cells have excellent therapeutic effects in vivo.

Moreover, the immune cells comprising the chimeric antigen receptor of the present application exhibit excellent targeting in vitro. They have a very strong killing ability on cells that positively express BCMA, and substantially no killing effect on cells that do not express BCMA. In addition, they also exhibit excellent tumor targeting in the in vivo experiments.

DETAILED DESCRIPTION OF THE EMBODIMENTS

Figure 1:
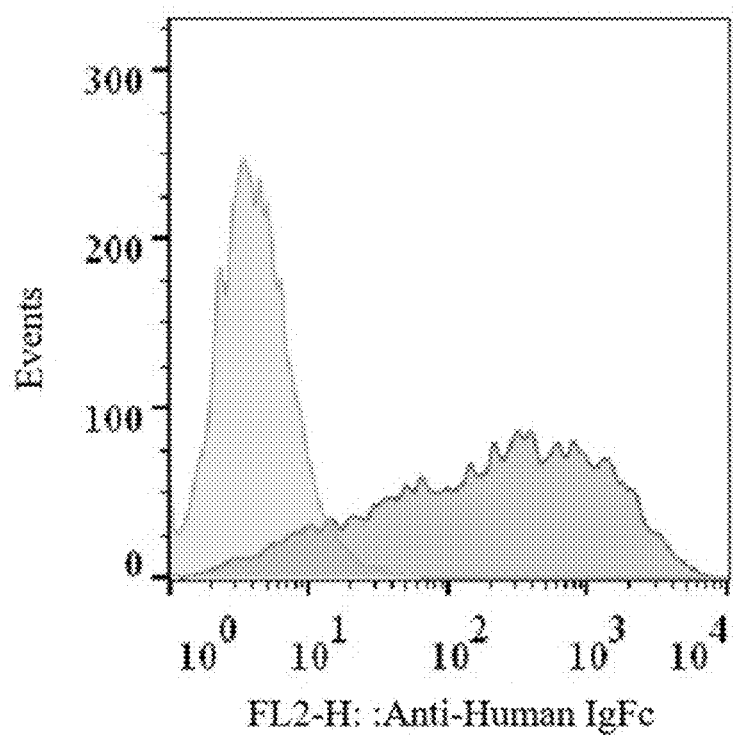
FIG. 1 shows a flow cytometry result of the expression of the chimeric antigen receptor in the immune cells comprising the chimeric antigen receptor of the present application.

The applicant has designed a specific single domain antibody as an antigen binding region of CAR for CAR modification and CART cell therapy by means of genetic engineering, and proposed a specific chimeric antigen receptor (CAR) based on a single domain antibody including an extracellular domain, a transmembrane domain, and an intracellular domain, wherein the extracellular domain is an antigen binding fragment that can bind to human BCMA (B cell mature antigen) selected from Alpaca single domain antibody (sdAb, nano antibody).

In the present application, the term "CDR" generally refers to a complementary determining region which is mainly responsible for binding to antigen epitopes. The CDRs of heavy chain are generally called HCDR1, HCDR2, and HCDR3, which are sequentially numbered from the N-terminal. In the present application, the CDRs can be defined or identified by conventional means, e.g., according to the method disclosed in Kabat et al. (Wu, T T, and Kabat, E. A., J Exp Med. 132 (2):211-50, (1970); Borden, P., and Kabat E. A., PNAS, 84:2440-2443 (1987), or the method disclosed in Chothia et al. (Chothia, C., and Lesk, A. M., J Mol. Biol., 196 (4):901-917 (1987).

In the present application, the term "single domain antibody (sdAb)" generally refers to an antibody fragment composed of a variable region of an antibody heavy chain (VH domain), or a variable region of an antibody light chain (VL domain) (Holt, L. et al., Trends in Biotechnology, 21 (11):484-490), which is also known as Nanobody. The single domain antibody is only about 12-15 kDa. The first single domain antibody, also known as "VHH segment", was prepared by artificial engineering from the heavy chain antibody of alpaca. In the present application, the single domain antibody can be a single domain antibody of alpaca. For example, the VHH segment can refer to the known minimum antigen binding unit of the heavy chain antibody (Koch-Nolte et al., FASEB J., 21:3490-3498 (2007)).

In the present application, the term "transmembrane domain" can be interchangeably used with "transmembrane region (briefly, TM)", and refers to a part of the CAR which fuses the extracellular binding portion to the intracellular signaling domain, and anchors the CAR to the plasma membrane of immune effector cells. The transmembrane region can be either derived from naturally occurring proteins, or obtained by synthesis, semi-synthesis, or recombination. The TM domain can include at least the transmembrane domain of the following proteins: α-, μ-, or ζ-chain of a T cell receptor, CD3ε, CD3ζ, CD4, CD5, CD8a, CD9, CD16, CD22, CD27, CD28, CD33, CD37, CD45, CD64, CD80, CD86, CD134, CD137, CD152, CD154, and PD1. In the present application, the transmembrane domain can include a polypeptide derived from a protein selected from a, 0, or (chain of a T-cell receptor, CD28, CD3e, CD45, CD4, CD5, CD8a, CD9, CD16, CD22, CD33, CD37, CD64, CD80, CD86, CD134, CD137, and CD154.

In the present application, the term "intracellular signaling domain" is generally a part of the CAR which is involved in the transduction of information of effective anti-BCMA CAR binding to human BCMA polypeptide into the interior of immune effector cells, so as to trigger the functions of the effector cells, e.g., activation, production of cytokines, proliferation, and cytotoxic activity, including the release of cytotoxic factors to the CAR-binding target cells, or other cell responses induced by antigens binding to the extracellular CAR domain. In the present application, the intracellular signaling domain can comprise a signaling domain of CD3ζ.

In the present application, the term "BCMA" generally refers to a cellular mature antigen which belongs to a member of tumor necrosis factor receptor superfamily (see, Thompson et al., J. Exp. Medicine, 192 (1):129-135, 2000). BCMA can bind to B cell activation factors (BAFFs) and proliferation inducing ligands (APRILs) (see Kalled et al., Immunological Reviews, 204:43-54, 2005). In non-malignant cells, it has been reported that BCMAs are mainly expressed in a subset of plasmacytes, and mature B cells (see Laabi et al., EMBO J., 77 (1):3897-3904, 1992; Laabi et al., Nucleic Acids Res., 22 (7):1147-1154, 1994; Kalled et al., 2005; O'Connor et al., J. Exp. Medicine, 199 (1):91-97, 2004; and Ng et al., J. Immunol., 73 (2):807-817, 2004). BCMA RNAs are commonly detected in multiple myeloma cells and other lymphomas, and some researchers have detected the BCMA protein on the surface of plasmacytes from patients with multiple myeloma (see Novak et al., Blood, 103 (2):689-694, 2004; Neri et al., Clinical Cancer Research, 73 (19):5903-5909, 2007; Bellucci et al., Blood, 105 (10):3945-3950, 2005; and Moreaux et al., Blood, 703 (8):3148-3157, 2004). Thus, BCMA can be used as a potential therapeutic target of malignant tumors (e.g., multiple myeloma).

In the present application, the term "BCMA binding domain" generally refers to including a humanized anti-BCMA antibody which can specifically bind to the BCMA polypeptide expressed on B cells, or an antigen binding fragment thereof. In the present application, the binding domain can be derived from naturally occurring sources, synthetic sources, semi-synthetic sources, or recombinant sources. In the present application, the extracellular binding domain can include an antibody against BCMA, or an antigen binding fragment thereof. Of those, the "antibody" can be a polypeptide including at least a light chain or a heavy chain immunoglobulin variable region which specifically recognizes and binds to an epitope of an antigen (e.g., BCMA), such as, antigenic determinant-containing peptides, lipids, polysaccharides, or nucleic acids (e.g., those recognized by immune cells).

In the present application, the term "co-stimulatory domain" generally refers to an intracellular signaling domain of a co-stimulatory molecule. For example, the co-stimulatory molecule can be a cell surface molecule other than antigen receptor or Fc receptor which can provide a second signal required by the effective activation and functions of T lymphocytes. For example, the co-stimulatory domain can be selected from the group consisting of CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70.

In the present application, the term "hinge region" generally refers to a domain in a chimeric antigen receptor that locates the binding domain away from the surface of effector cells so as to play a proper role in cell/cell contact, antigen binding and activation. In the present application, the hinge region can be located between the binding domain and the transmembrane domain. The hinge region can be derived from naturally occurring sources, synthetic sources, semi-synthetic sources, or recombinant sources. The hinge domain can comprise an amino acid sequence of a naturally occurring immunoglobulin hinge region or an artificially modified (including deleted, substituted, or inserted) immunoglobulin hinge region.

In the present application, the term "leader sequence" generally refers to a sequence located before the coding region of the structural gene that can be transcribed but cannot be translated. In the present application, the leader sequence can start from the 5' end to the first coder of the gene encoding the chimeric antigen receptor. In the present application, the leader sequence comprises an amino acid sequence as set forth in SEQ ID NO:9 or a functional variant thereof.

In the present application, the term "functional variant" generally refers to an amino acid sequence having substantially the same functions therewith (e.g., having the properties of the chimeric antigen receptor), and having at least 85% (e.g., at least 85%, at least 90%, at least 91%, at least 92%, at least 93%, at least 94%, at least 95%, at least 96%, at least 97%, at least 98%, at least 99%, or at least 100%) sequence identity therewith. In some embodiments, the variant of the amino acid sequence is an amino acid sequence having substantially the same functions therewith (e.g., having the properties of the chimeric antigen receptor), and including one or more (e.g., 1-2, 1-3, 1-4, 1-5, 1-6, 1-7, 1-8, 1-9, 1-10, or more) substitutions, deletions, or additions of amino acids on the basis of the amino acid sequence.

In the present application, the term "lentiviral vector" generally refers to a gene therapy vector developed on the basis of virus. In the present application, the virus can be human immunodeficiency virus (HIV), simian immunodeficiency virus (SIV), equine infectious anemia (EIA), or feline immunodeficiency virus (FIV). The lentiviral vector has the ability to infect both mitotic cells and non-mitotic cells, can effectively infect almost all the mammalian cells including neurons, hepatocytes, cardiomyocytes, tumor cells, endothelial cells, stem cells and the like, and has high infection efficiency.

In the present application, the term "EF1 promoter" generally refers to a promoter that can constantly keep the transcriptional level of the regulated target gene at a certain level. In the present application, the EF1 promoter can comprise a sequence as set forth in SEQ ID NO:14. In the present application, the expression level of the chimeric antigen receptor regulated by the EF1 promoter can be upregulated or down-regulated by at most 5%, at most 4%, at most 3%, at most 2%, at most 1%, at most 0.5%, at most 0.1%, at most 0.01%, or less. In the present application, the EF1 promoter can be located upstream of the nucleic acid encoding the chimeric antigen receptor.

In the present application, the term "T lymphocytes" generally refers to those including thymocytes, immature T lymphocytes, mature T lymphocytes, resting T lymphocytes, or activated T lymphocytes. T cells can be helper T (Th) cells, such as, helper T1 (Th1) cells, or helper T2 (Th2) cells. T cells can be helper T cells (HTL; CD4$^+$T cells) CD4$^+$T cells, cytotoxic T cells (CTL; CD8$^+$T cells), CD4$^+$CD8$^+$T cells, or CD4$^-$CD8$^-$T cells. Alternatively, the T lymphocytes can include native T cells and memory T cells.

In the present application, the term "natural killer cells" generally refers to a subtype of white blood cells which is a component of the innate immune system. NK cells play an important role in host rejection of tumors and virus-infected cells. NK cells have cytoxicity and induce the apoptosis. NK cells can be used to inhibit virus infection, and produce antigen-specific cytotoxic T cells by adaptive immune response, thereby eliminating infection.

In the present application, the term "tumor" generally refers to neogrowths formed by the clonal abnormal proliferation of a certain cell in local tissue that loses the normal growth regulation at the gene level under the action of various carcinogenic factors. It is also called neoplasm because such neogrowth mostly presents occupying massive bumps. In the present application, the cancer can include squamous cell carcinoma, lung cancer (including small cell lung cancer, non-small cell lung cancer, lung adenocarcinoma, and lung squamous cell carcinoma), peritoneal carcinoma, hepatocellular carcinoma, gastric carcinoma or gastric cancer (including gastrointestinal cancer), pancreatic cancer, glioblastoma, cervical cancer, ovarian cancer, liver cancer, bladder cancer, liver cancer, breast cancer, colon cancer, colorectal cancer, endometrial or uterine cancer, salivary gland cancer, kidney or renal cancer, liver cancer, prostate cancer, vulvar cancer, thyroid cancer, liver cancer, head and neck cancer, B-cell lymphoma (including low-grade/follicular NHL), small lymphocytic (SL) NHL, intermediate/follicular NHL, medium-grade diffuse NHL, advanced immunoblastic NHL, advanced lymphocytic NHL, advanced small non cleaved cell NHL, AIDS-related lymphoma, Waldenstrom's macroglobulinemia, chronic lymphocytic leukemia (CLL), acute lymphocytic leukemia (ALL), hairy cell leukemia, chronic myeloblastosis, and post-transplant lymphoproliferative disease (PTLD). In the present application, the cancer can comprise cancers or malignant tumors associated with the expression of BCMA. For example, the cancer can be selected from the group consisting of B cell acute lymphoblastic leukemia, T cell acute lymphoblastic leukemia, acute lymphoblastic leukemia, chronic myeloid leukemia, chronic lymphocytic leukemia, B cell prolymphocytic leukemia, blast cell plasmacytoid dendritic cytoma, Burkitts lymphoma, diffuse large B cell lymphoma, follicular lymphoma, hairy cell leukemia, small or large cell follicular lymphoma, malignant lymphoproliferative condition, MALT lymphoma, mantle cell lymphoma, marginal zone lymphoma, multiple myeloma, myelodysplasia, and myelodysplastic syndrome, non-Hodgkin lymphoma, plasmablast lymphoma, plasmacytoid dendritic cytoma, Waldenstrom macroglobulinemia, prostatic cancer, pancreatic cancer, lung cancer, myeloma, MGUS, plasmacytoma, systemic amyloid light chain amyloidosis, and POEMS syndrome.

The present application provides a chimeric antigen receptor (CAR) comprising a BCMA binding domain, a transmembrane domain, one or more co-stimulatory domain, and an intracellular signaling domain; wherein the BCMA binding domain includes a heavy chain complementary determining region 1 (HCDR1), a heavy chain complementary determining region 2 (HCDR2), and a heavy chain complementary determining region 3 (HCDR3), wherein the amino acid sequence of the HCDR1 is as set forth in SEQ ID NO: 1, the amino acid sequence of the HCDR2 is as set forth in SEQ ID NO: 2, and the amino acid sequence of the HCDR3 is as set forth in SEQ ID NO: 3.

In the present application, the BCMA binding domain can bind to or be associated with BCMA with $K_a$ (that is, an equilibrium association constant of binding interaction at 1/M) of greater than or equal to about $10^5 M^{-1}$ (e.g., greater than or equal to about $10^5 M^{-1}$, greater than or equal to about $10^6 M^{-1}$, greater than or equal to about $10^7 M^{-1}$, greater than or equal to about $10^8 M^{-1}$, greater than or equal to about $10^9 M^{-1}$, greater than or equal to about $10^{10} M^{-1}$, greater than or equal to about $10^{11}M^{-1}$, greater than or equal to about $10^{12}M^{-1}$, greater than or equal to about $10^{13}M^{-1}$ or greater), or with a dissociation equilibrium constant $K_d$ of less than or equal to about $10^{-5}M$ (e.g., less than or equal to about $10^{-5}M$, less than or equal to about $10^{-6}M$, less than or equal to about $10^{-7}M$, less than or equal to about $10^{-1}M$, less than or equal to about $10^{-9}M$, less than or equal to about $10^{-10}M$, less than or equal to about $10^{-11}M$, less than or equal to about $10^{-12}M$, less than or equal to about $10^{-13}M$ or less).

In the present application, the affinity between the BCMA binding domain and BCMA can be determined by conventional techniques in the art, for example, by competitive ELISA (enzyme-linked immunosorbent assay), or by binding association, or by displacement assay using labeled ligands, or by using surface plasmon resonance (such as Biacore T100, which can be obtained from Biacore, Inc., Piscataway, NJ), or optical biosensor technology.

In the present application, the BCMA binding domain can be a single domain antibody. The BCMA binding domain suitable for constructing the chimeric antigen receptor of the present application includes, but is not limited to, an amino acid sequence as set forth in SEQ ID NO:4 or a functional variant thereof. Of those, the functional variant is selected from the group consisting of proteins or polypeptides formed by substituting, deleting or adding one or more amino acids in the BCMA binding domain; and proteins or polypeptides having 90% or above (e.g., at least about 90%, about 91%, about 92%, about 93%, about 94%, about 95%, about 96%, about 97%, about 98%, about 99% or greater) sequence homology with the BCMA binding domain.

In the present application, the transmembrane domain can comprise a polypeptide derived from a protein selected from the group consisting of α, β, or ζ chain of a T-cell receptor, CD28, CD3ζ, CD45, CD4, CD5, CD8a, CD9, CD16, CD22, CD33, CD37, CD64, CD80, CD86, CD134, CD137, and CD154. In the present application, the transmembrane domain can be derived from transmembrane domain of CD8α. In the present application, the transmembrane domain can comprise an amino acid sequence as set forth in SEQ ID NO:5 or a functional variant thereof. Of those, the functional variant is selected from the group consisting of proteins, or polypeptides formed by substituting, deleting, or adding one or more amino acids in the transmembrane domain; and proteins, or polypeptides having 90%, or above (e.g., at least about 90%, about 91%, about 92%, about 93%, about 94%, about 95%, about 96%, about 97%, about 98%, about 99% or greater) sequence homology with the transmembrane domain.

In the present application, the BCMA binding domain can be linked to the transmembrane domain via a hinge region. In the present application, the CAR can comprise one or more of the hinge regions between the BCMA binding domain and the transmembrane domain. The hinge region can comprise some mutations, or substitutions of amino acids, e.g., those in which a proline residue is mutated to, or substituted with another amino acid residue (e.g., a serine residue). In the present application, the hinge region can comprise an amino acid sequence as set forth in SEQ ID NO:6 or a functional variant thereof. Of those, the functional variant is selected from the group consisting of proteins or polypeptides formed by substituting, deleting or adding one or more amino acids of the hinge region; and proteins or polypeptides having 90% or above (e.g., at least about 90%, about 91%, about 92%, about 93%, about 94%, about 95%, about 96%, about 97%, about 98%, about 99%, or greater) sequence homology with the hinge region.

In the present application, the co-stimulatory domain can function in an antigen-independent (e.g., BCMA-independent) manner to provide a secondary, or co-stimulatory signal. In the present application, the CAR can comprise one or more of the co-stimulating domains. The plurality of co-stimulatory domains can enhance the potency, and multiplication capacity of immune cells (e.g., T cells, and NK cells) expressing the CAR. For example, the co-stimulatory domain can be linked to the C-terminal of the transmembrane domain. In the present application, the one or more of the co-stimulatory domains can be derived from a co-stimulating molecule selected from CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKG2C, SLP76, TRIM, and ZAP70. In the present application, the co-stimulatory domain can be derived from CD137. In the present application, the co-stimulatory domain can comprise an amino acid sequence as set forth in SEQ ID NO:7 or a functional variant thereof. Of those, the functional variant is selected from the group consisting of proteins or polypeptides formed by substituting, deleting or adding one or more amino acids in the co-stimulatory domain; and proteins or polypeptides having 90% or above (e.g., at least about 90%, about 91%, about 92%, about 93%, about 94%, about 95%, about 96%, about 97%, about 98%, about 99% or greater) sequence homology with the co-stimulatory domain.

In the present application, the intracellular signaling domain can be primarily activated by TCR (e.g., TCR/CD3 complex) in an antigen-dependent manner. In the present application, the intracellular signaling domain can be derived from TCRζ, FcRγ, FcRβ, CD3γ, CD3δ, CD3ε, CD3ζ, CD22, CD79a, CD79b, and CD66d. In the present application, the intracellular signaling domain can comprise a signaling domain of CD3ζ. For example, the intracellular signaling domain comprises an amino acid sequence as set forth in SEQ ID NO:8 or a functional variant thereof. Of those, the functional variant is selected from the group consisting of proteins or polypeptides formed by substituting, deleting or adding one or more amino acids in the intracellular signaling domain; and proteins or polypeptides having 90% or above (e.g., at least about 90%, about 91%, about 92%, about 93%, about 94%, about 95%, about 96%, about 97%, about 98%, about 99% or greater) sequence homology with the intracellular signaling domain.

In the present application, the CAR can further include a leader sequence. For example, the leader sequence can comprise an amino acid sequence as set forth in SEQ ID NO:9 or a functional variant thereof. Of those, the functional variant is selected from the group consisting of proteins or polypeptides formed by substituting, deleting or adding one or more amino acids in the leader sequence; and proteins or polypeptides having 90% or above (e.g., at least about 90%, about 91%, about 92%, about 93%, about 94%, about 95%, about 96%, about 97%, about 98%, about 99%, or greater) sequence homology with the leader sequence.

In the present application, the CAR can comprise a linker between respective domains. For example, a linker is incorporated for achieving a proper spacing and configuration between respective domains. For example, the linker can link the transmembrane domain to the intracellular signaling domain. In the present application, the linker can comprise the following amino acid sequences: GGG, $(GGGGS)_n$, and GGRRGGGS.

In the CAR of the present application, the transmembrane domain can be derived from CD8α, the co-stimulatory domain can be derived from CD137, and the intracellular signaling domain can be derived from CD3ζ.

In the present application, the CAR can comprise a BCMA binding domain including an HCDR1 having an amino acid sequence as set forth in SEQ ID NO:1, an HCDR2 having an amino acid sequence as set forth in SEQ ID NO:2, and an HCDR3 having an amino acid sequence as set forth in SEQ ID NO:3, a transmembrane domain having an amino acid sequence as set forth in SEQ ID NO:5, a hinge region having an amino acid sequence as set forth in SEQ ID NO:6, a co-stimulatory domain having an amino acid sequence as set forth in SEQ ID NO:7, an intracellular signaling domain having an amino acid sequence as set forth in SEQ ID NO:8, and a leader sequence having an amino acid sequence as set forth in SEQ ID NO:9.

In the present application, the CAR can comprise a BCMA binding domain including an amino acid sequence as set forth in SEQ ID NO:4, a transmembrane domain including an amino acid sequence as set forth in SEQ ID NO:5, a hinge region including an amino acid sequence as set forth in SEQ ID NO:6, a co-stimulatory domain including an amino acid sequence as set forth in SEQ ID NO:7, an intracellular signaling domain including an amino acid sequence as shown in SEQ ID NO:8, and a leader sequence including an amino acid sequence as set forth in SEQ ID NO:9.

In present application, the CAR comprises an amino acid sequence as set forth in SEQ ID NOs:10-11 or a functional variant thereof. Of those, the functional variant is selected from the group consisting of proteins or polypeptides formed by substituting, deleting or adding one or more amino acids in the CAR; and proteins or polypeptides having 90% or above (e.g., at least about 90%, about 91%, about 92%, about 93%, about 94%, about 95%, about 96%, about 97%, about 98%, about 99% or greater) sequence homology with the CAR.

The present application provides an isolated nucleic acid molecule which can encode the CAR.

In the present application, the nucleic acid molecule can comprise a nucleic acid sequence as set forth in SEQ ID NOs:12-13 or a functional variant thereof. For example, the functional variant can include a polynucleotide having at least about 50%, 55%, 60%, 65%, 70%, 75%, 80%, 85%, 90%, 95%, 96%, 97%, 98%, 99%, or 100% sequence identity with the sequence of SEQ ID NOs:12-13, or a variant, as long as it can still encode the CAR.

The present application provides a vector which can comprise the nucleic acid molecule.

In the present application, the vector can include one or more of replication origin, selection box, promoter, enhancer, translation initiation signal (Shine Dalgarno sequence, or Kozak sequence), intron, polyadenylation sequence, 5' and 3' untranslated region. For example, the vector can comprise an EF1 promoter and the EF1 promoter can comprise a sequence as set forth in SEQ ID NO:14. In the present application, the vector can be selected from plasmids, phages, artificial chromosomes (e.g., yeast artificial chromosome, YAC), and animal virus. For example, the vector can be selected from DNA vectors, RNA vectors, plasmids, lentiviral vectors, adenoviral vectors, and retroviral vectors.

The present application provides an immune effector cell which can comprise the CAR, the nucleic acid molecule, or the vector.

In the present application, the immune effector cell can be selected from T lymphocytes, and natural killer (NK) cells.

In the present application,

The present application provides a method of preparing an immune effector cell including introducing the vector into an immune effector cell. For example, the CAR is introduced into and expressed in the immune cells, so as to re-target the CAR specifically to the target antigen (e.g., BCMA). In the present application, the immune effector cell can be selected from T lymphocytes, and natural killer (NK) cells. In the present application, the method can include a step of obtaining immune effector cells from a subject. For example, the T lymphocytes can be obtained from peripheral blood mononuclear cells, bone marrow, lymph node tissue, umbilical cord blood, thymus tissue, tissue from the site of infection, ascites, pleural effusion, spleen tissue, and tumor. Moreover, the method can further include a step of selecting a specific cell subset from the immune effector cell. For example, a specific T cell subset can be selected in accordance with the specific expression of CD3, CD28, CD4, CD8, CD45RA, and CD45RO.

The present application provides a composition which can comprise the immune effector cell.

In the present application, the composition can comprise pharmaceutically acceptable carriers. The pharmaceutically acceptable carriers can be selected from the group consisting of excipients, glidants, sweeteners, diluents, preservatives, dyes/colorants, flavor enhancers, surfactants, wetting agents, dispersants, suspension agents, stabilizers, isotonic agents, solvents, surfactants, and emulsifiers.

In the present application, the composition can further include additional active ingredients, such as, one or more of cytokines, growth factors, hormones, small molecular chemical active ingredients, prodrugs, and antibodies.

In the present application, the amount of the immune effector cells in the composition can be the effective amount. The effective amount can be the minimum amount that can achieve the beneficial, or desired prophylactic, or therapeutic effect. For example, the effective amount can be influenced by the severity of disease, age, weight, sex, or other factors of the subject.

The present application provides use of the CAR, the nucleic acid molecule, the vector, or the immune effector cell in manufacture of a drug for treating a disease or disorder associated with the expression of BCMA.

The present application provides the CAR, the nucleic acid molecule, the vector or the immune effector cell for treating a disease or disorder associated with the expression of BCMA.

The present application provides a method of treating a disease or disorder associated with the expression of BCMA including the step of administering the CAR, the nucleic acid molecule, the vector or the immune effector cell to a subject.

In the present application, the disease or disorder associated with the expression of BCMA is cancer or malignant tumor. In the present application, the disease or disorder associated with the expression of BCMA is selected from the group consisting of B cell acute lymphoblastic leukemia, T cell acute lymphoblastic leukemia, acute lymphoblastic leukemia, chronic myeloid leukemia, chronic lymphocytic leukemia, B cell prolymphocytic leukemia, blast cell plasmacytoid dendritic cytoma, Burkitt's lymphoma, diffuse large B cell lymphoma, follicular lymphoma, hairy cell leukemia, small or large cell follicular lymphoma, malignant lymphoproliferative condition, MALT lymphoma, mantle cell lymphoma, marginal zone lymphoma, multiple myeloma, myelodysplasia, and myelodysplastic syndrome, non-Hodgkin lymphoma, plasmablast lymphoma, plasmacytoid dendritic cytoma, Waldenstrom macroglobulinemia, prostatic cancer, pancreatic cancer, lung cancer, myeloma, MGUS, plasmacytoma, systemic amyloid light chain amyloidosis, and POEMS syndrome.

In the present application, the administration mode of the drug can include aerosol inhalation, injection, ingestion, infusion, implantation, or transplantation. For example, the injection can include intravascular, intravenous, intramuscular, intraarterial, intrathecal, intracapsular, intraorbital, intratumoral, intracardiac, intradermal, intraperitoneal, transtracheal, subcutaneous, subepidermal, intraarticular, subcapsular, subarachnoid, intraspinal, and intrasternal injections, or can be direct injection into tumor or lymph node.

Hereinafter the present application is further illustrated by detailed examples. It should be understood that the following examples are merely for the purpose of illustrating the present application, and do not limit the content of the invention.

EXAMPLES

Example 1 Obtainment of VHH Gene of BCMA Single Domain Antibody

1) Construction of BCMA Single Domain Antibody Library

Healthy adult alpacas were immunized by subcutaneous multiple injections in the neck and back with the BCMA antigen purchased from Beijing Yiqiao Shenzhou Ltd. Upon immunization, the antigen and an equal volume of Freund's adjuvant were added for 4-6 immunizations. The mass absorption at the injection sites were tracked and observed to confirm the correct immunization. The interval between immunizations was 7-15 days. After the fourth immunization, blood samples were collected to determine the immune titer of the antigen. When the titer reached more than 10000 times (ELISA method), a blood sample (about 100 ml) was collected to isolate lymphocytes for extracting RNAs, which were reverse transcribed to cDNA. The variable region fragment VHH of alpaca heavy chain antibody was amplified by PCR for twice. The VHH fragment was constructed into the phage display library, and the product of gene fragment carrying a single domain antibody was transformed into competent cells, so as to obtain a single domain antibody immune library.

2) Screening of BCMA Single Domain Antibody

Single domain antibody molecules were displayed on the surface of phage by a phage display technology, and then screened to obtain antigen-specific single domain antibodies. By phage enzyme linked immunosorbent assay (ELISA), the antigen was diluted with 100 mM NaHCO$_3$ (pH 8.0) to a final concentration of 100 μg/mL, and 100 μL was coated into a 96-well plate, stood overnight at 4° C. After washing with PBS, and sealing with 1% skim milk, the phages were added to incubate for 1-2 hours. Then, the antigen-specific phages were eluted, and infected TG1 cells, which were coated and cultured on an LB culture plate containing ampicillin. By several rounds of screening, concentration was gradually achieved. A large number of positive clones were selected for ELISA detection, and the positive clones were sequenced. According to the sequence alignment, the unique clones were identified, and divided into the frame region (FR), and the complementary determining region (CDR).

The clones with correct sequencing were inoculated in 5 mL of LB medium containing ampicillin, and cultured overnight at 37° C. in a shaker. 1 mL of bacterial solution was inoculated into 300 mL of LB medium, and cultured at 37° C. in a shaker until OD$_{600nm}$=0.6-0.9. 1M IPTG was added and cultured overnight at 28° C. in a shaker. The bacteria were collected by centrifugation. The crude extract of antibody was obtained by using an osmotic method. The single domain antibody was labeled by ProteinL, and purified by affinity chromatography with a yield of more than 10 mg/L. The antibody affinity was detected by SPR technology for further screening the single domain antibodies with high specificity. By the above embodiment, a total of 6 BCMA single domain antibodies were obtained, and the single domain antibody with higher affinity was selected.

Of those, one BCMA single domain antibody is named BCMA sdAb I. By sequencing, it is found that the amino acid sequences of HCDR1-3 of BCMA sdAb I are sequentially as set forth in SEQ ID NOs: 1-3.

Example 2 Construction of Chimeric Antigen Receptor Gene Vector

Two gene segments were synthesized by Taihe Biotechnology Co., Ltd. One is the nucleotide sequence of SEQ ID NO. 15 contained in the BCMA sdAb I prepared in Example 1; and the other is a designed generation 2 CAR structural gene (CD8a hinge region, transmembrane domain+4-1BB co-stimulatory domain+CD3ζ intracellular signaling domain, and the nucleotide sequence of encoding the generation 2 CAR structural gene containing these domains is as set forth in SEQ ID NO: 16). After obtaining the synthetic gene, a molecular cloning was performed to construct the BCMA CAR. The PCR products of SEQ ID NO: 15, and SEQ ID NO: 16 were obtained by PCR. The overlapping PCR was used to obtain the BCMA CAR gene formed by linking the two fragments (its nucleotide sequence is as set forth in SEQ ID NO: 12). The lentivirus Pre vector and the BCMA CAR gene were digested by enzyme, connected, and transformed. Clones were picked up, and plasmids were extracted. Sequencing was performed to obtain the correct sequence of lentiviral vector Pre-Lenti-EF1-BCMA.

1) SEQ ID NO: 15:
atggccttaccagtgaccgccttgctcctgccgctggccttgctgctcca cgccgccaggccggaagtccaactccaggcttccggtggcggtctggcac agcctggagggtccctgcggctctcctgcgcagcaagtggcaggactttc agtacctactttatggcctggttcagacagccacctggcaaaggcctcga atacgtcggagggattaggtggtctgacggtgtccctcactacgctgaca gtgtgaagggtcggttcaccattagcagagacaacgctaagaatacagtg tacctgcaaatgaactcactgagagctgaggatactgagtgtacttctgc gcatctcgcggaatcgctgacgggtcagactttggctcctatggacaggg cacccaggtgactgtgagttcc 2) SEQ ID NO: 16:
ccagcgaagccaccacgacgccagcgccgcgaccaccaacaccggcgcc caccatcgcgtcgcagccctgtccctgcgcccagaggcgtgccggccagc ggcgggggcgcagtgcacacgaggggctggacttcgcctgtgatatct acatagggcgcccttggccgggattgtggggtccttctcctgtcactggt tatcaccctttactgcaaacggggcagaaagaaactcctgtatatattca -continued

```
aacaaccatttatgagaccagtacaaactactcaagaggaagatggctgt agctgccgatttccagaagaagaagaaggaggatgtgaactgagagtgaa gttcagcaggagcgcagacgccccgcgtaccagcagggccagaaccagc tctataacgagctcaatctaggacgaagagaggagtacgatgttttggac aagagacgtggccgggaccctgagatgggggggaaagccgcagagaaggaa gaaccctcaggaaggcctgtacaatgaactgcagaaagataagatggcgg aggcctacagtgagattgggatgaaaggcgagcgccggaggggcaagggg cacgatggcctttaccagggtctcagtacagccaccaaggacacctacga cgccttcacatgcaggcctgcccctcgctaa
```

Example 3 Preparation of Lentivirus of BCMA Chimeric Antigen Receptor

On the day before virus packaging, 293T cells (purchased from ATCC) were digested by trypsin, and inoculated into a 10 cm dish at $1 \times 10^7$ cells/dish. Upon transfection of cells, in addition to the Pre-Lenti-EF1-BCMA plasmid prepared in Example 2, each plasmid needed to be co-transfected with packaging plasmids psPAX2, pMD2.0G. Of those, 5 μg of the Pre-Lenti-EF1-BCMA, 3.75 μg of the psPAX2 plasmid, and 1.25 μg of the pMD2.0G plasmid were used. Upon transfection, a mixture of the above three plasmids was added into 500 μl MEM medium. In a separate micro-centrifuge tube, 25 μL of Lipofectamine (liposome) 2000 reagent was added into 500 μl MEM medium. Then, the diluted transfection reagent was added dropwise above the diluted plasmid, mixed well, centrifuged, and stood at room temperature for 20 minutes. Finally, the mixture of plasmid and transfection reagent was added into 10 cm culture dish, shaken gently for 10 times, mixed well, and placed into an incubator. After 3 days of transfection, the virus was harvested. 10 ml of virus containing culture supernatant was transferred into a 50 ml centrifuge tube, and centrifuged at 4° C. at 1250 rpm for 5 minutes to remove dead 293T cells. Then, the virus containing supernatant was filtered, concentrated, subpackaged, and stored at −80° C. for use.

Example 4 Preparation of T Cells Modified by BCMA Specific Chimeric Antigen Receptor 1) Preparation of T Lymphocytes In a sterile environment, 10 ml of venous blood was drawn from volunteers. To a 50 ml centrifuge tube was added 10 ml human lymphocyte isolates (Dakewei Bioengineering Co., Ltd.). The blood was slowly added with an electric pipette gun into the centrifuge tube along the wall. The centrifuge tube was placed into the centrifuge tube, and centrifuged at 700 g at 22° C. for 25 minutes. After completion of centrifugation, the PBMC was concentrated in the white membrane layer between the upper plasma layer and the separate solution. The white membrane layer was sucked into another centrifuge tube with a pasteur pipet (adding 30 ml of 1640 medium) as much as possible. Be careful not to suck the separated solution. 250 g, 22° C., 10 minutes. The upper liquid was discarded. The cells were re-suspended in 3 ml of 1640 medium, and counted for T cell purification.

$1 \times 10^7$ cells were placed in a micro-centrifuge tube, and centrifuged at 250 g at 22° C. for 10 minutes. The upper liquid was discarded, and the cell precipitates were re-suspended in 80 μL of magnetic bead separation buffer, and 20 μl of CD3MicroBeads (Meitianni) was added. The mixture was placed at 4° C. in a refrigerator for 1 hour to ensure sufficient binding. After 1 hour, 1 mL of magnetic bead separation buffer was added into the micro-centrifuge tube, and centrifuged at 250 g at 4° C. for 10 minutes. During this period, a filter column was prepared, and placed on a magnet, and rinsed with 500 μl buffer (the buffer flowed down with gravity). After centrifugation, the supernatant was discarded, and the cells were re-suspended in 500 μl buffer. The column was added, and the buffer flowed down with gravity. After the cell suspension flowed out, the column was washed four times with 500 μl buffer. The column was removed from the magnet, and the T cells were flushed out with 1 mL buffer into 1.5 ml micro centrifuge tube. The cells were centrifuged at 250 g at 4° C. for 10 minutes. The cells were re-suspended in an IL2-containing X-vivo 15 medium (Lonza), and inoculated at $2 \times 10^6$ T cells/well (in a 6-well place) after counting.

2) Infection of T Cells with Lentivirus

After culture overnight, the Pre-Lenti-EF1-BCMA virus solution with MOI=2 prepared in Example 3 was added for infection overnight. On Day 2, 1 ml of fresh medium was supplemented. On Day 3, the T cells had been sufficiently activated, and proliferated rapidly. At that time, the T cells were transferred into a 25 cm² culture flask. On Day 5 after infection, the expression efficiency of BCMA CAR molecules on the surface of T cells was determined with bio-labeled BCMA Fc protein to produce specific BCMA CART cells. The expression of CAR on the surface of cell membrane was detected by a flow cytometry. The flow cytometry detection results of the expression of BCMA CAR molecules on the surface of BCMA CART cells are shown in FIG. 1. The results in FIG. 1 show that the CAR expression efficiency in the BCMA CART cells prepared in example 4 is more than 50%.

Figure 2:
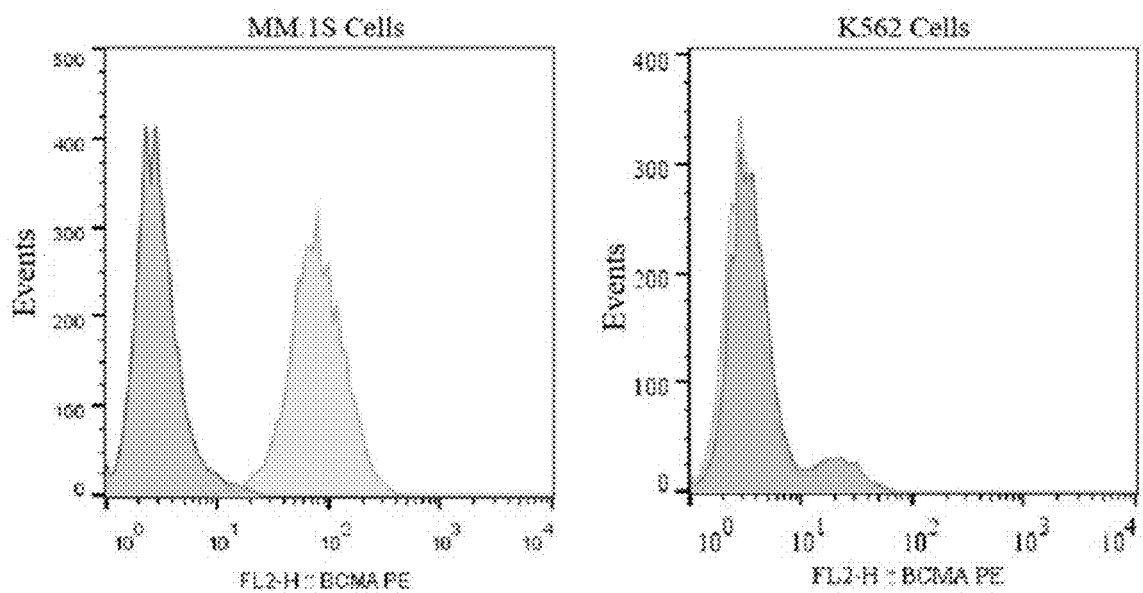
FIG. 2 shows a flow cytometry result of the BCMA expression abundance on the surface of multiple myeloma MM.1S cells (left panel), and myeloid leukemia K562 cells (right panel).

Example 5 Evaluation of Function of BCMA Chimeric Antigen Receptor-Modified T Cells 1) Evaluation of In Vitro Function Multiple myeloma MM.1S cells and myeloid leukemia K562 cells (purchased from ATCC were subject to flow cytometry. The results are shown in FIG. 2. The results of FIG. 2 indicate that BCMA molecules are effectively expressed in MM.1S cells, but not expressed in K562 cells.

In vitro cell killing experiments were performed by LDH detection kit (Promega) for detection. The BCMA CART cells prepared in Example 4 and target cells (such as, MM.1S cells or K562 cells) were set with four gradients according to the number ratio (i.e. multiplicity of infection), namely, 0.5:1, 1:1, 2:1, and 4:1. Of those, the target cells were $3 \times 10^4$ cells/well, and the systems in all the rest wells were supplemented to 200 μL with X-VIVO medium/1640 medium. The 96-well plate was incubated at 37° C., 5% $CO_2$ in an incubator. After 17 hours, 20 μL lysate was added into the well with maximum release. The cells were completely ruptured by mixing well. The 96-well plate was incubated in $CO_2$ in an incubator for 2 hours. After 2 hours, the well with maximum release was observed. After all the target cells were lysed, 50 μL of supernatant was collected from each well, and transferred into a 96-well flat bottom plate, and then 50 μL of substrate solution was added into each well, and developed in the dark for 30 minutes. After 30 minutes, the wells were observed for their color changes, wherein the well with maximum release of MM.1S and the well containing BCMA CART cells exhibited relatively dark colors. Measurements were made with an enzyme reader at a wavelength of 490 nm. The detection results of killing ability were obtained by using an LDH test kit.

Figure 3:
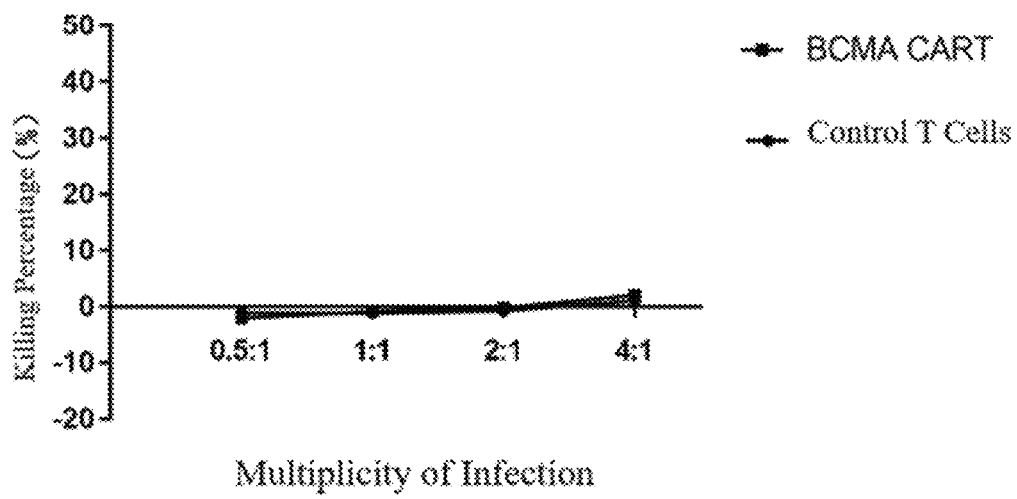
FIGS. 3A-3B show a result of the killing rate of target cells after co-incubation of tumor cells and the immune cells comprising the chimeric antigen receptor of the present application.
Figure 3:
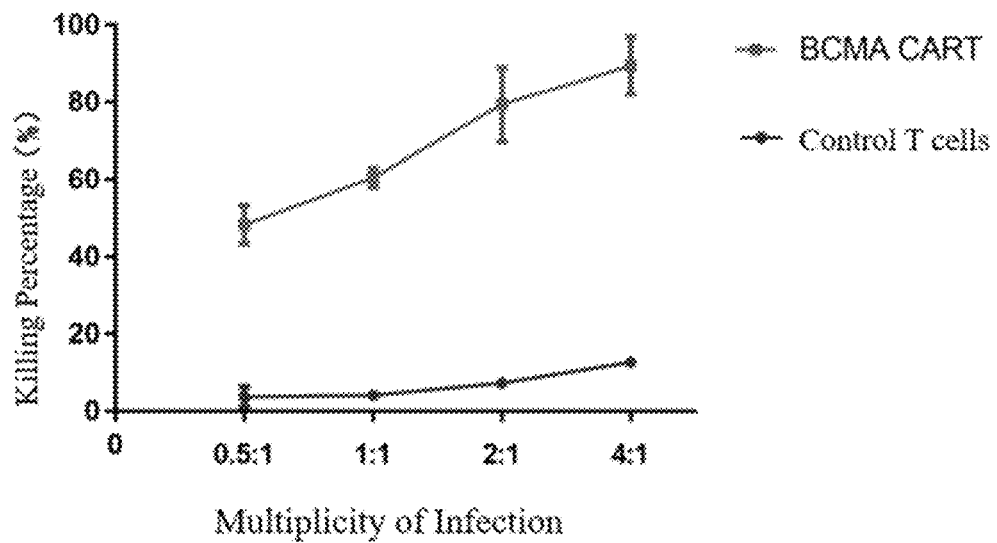

The results are shown in FIG. 3, the killing effect on K562 cells is shown in FIG. 3A; and the killing effect on MM.1S cells is shown in FIG. 3B. The results in FIG. 3 show that the BCMA CART cells prepared in Example 4 can specifically kill BCMA-positive cells with a high killing activity, such as, greater than 40%. At the same time, these BCMA CART cells produce no killing effect on BCMA-negative cells.

Figure 4:
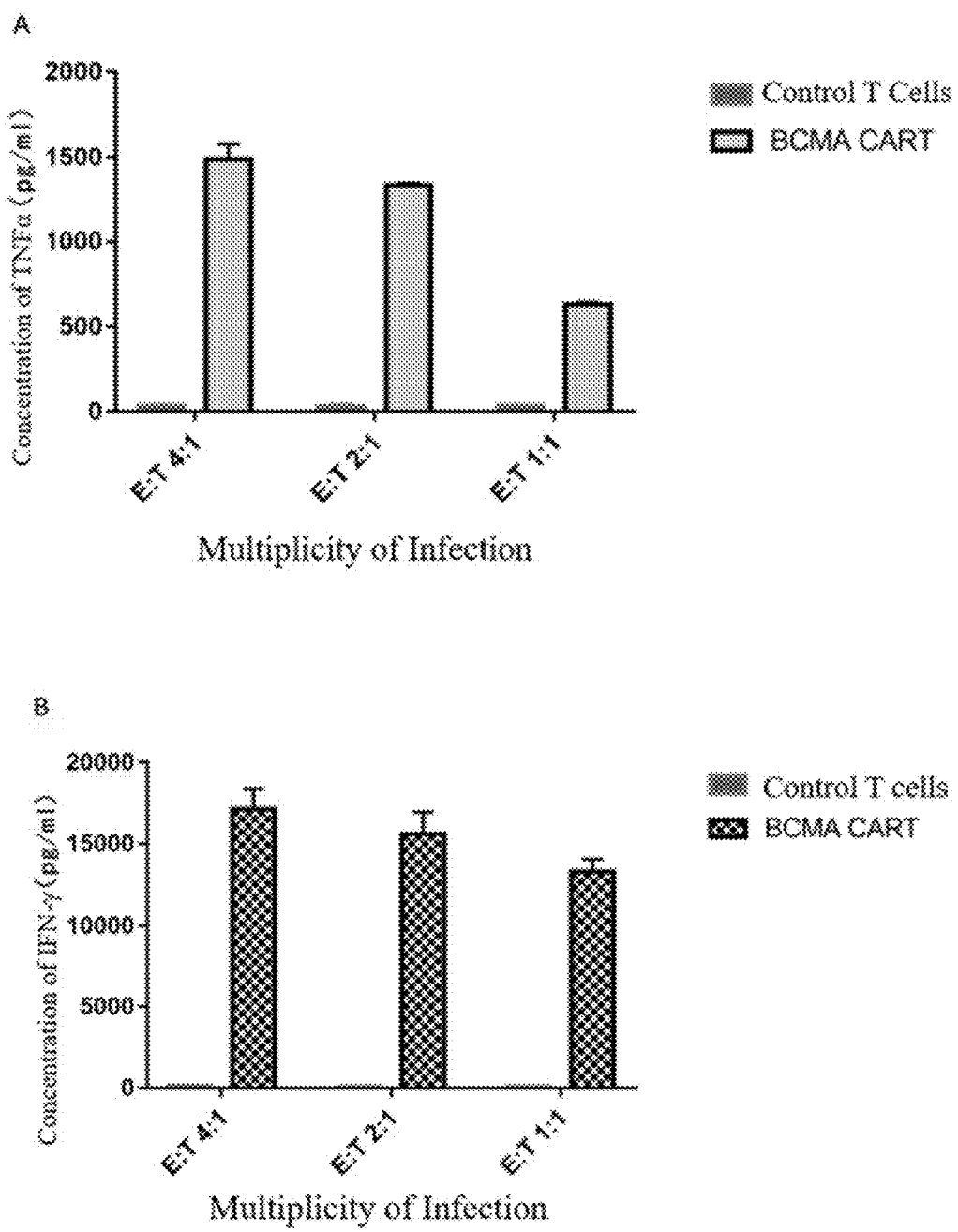
FIGS. 4A-4B show results of detecting the cytokine level in supernatant by an ELISA method after co-incubation of tumor cells and the immune cells comprising the chimeric antigen receptor of the present application.

The MM.1S tumor cells and the BCMA CART cells prepared in Example 4 were co-incubated, and detected by the ELISA method for the contents of IFN-γ and TNFα in the supernatant. The results are shown in FIG. 4, wherein the content of IFN-γ is shown in FIG. 4A, and the content of TNFα is shown in FIG. 4B. The results of FIG. 4 show that various multiplicities of infection can upregulate the expression levels of cytokines IFN-γ and TNFα having a tumor-killing effect. This proves the specific killing effect of BCMA CART cells from another viewpoint.

2) Animal Experiments

Human multiple myeloma cell line MM.1S was transduced to express the luciferase reporter gene to obtain MM.1S-luc. 1640 medium containing 10% fetal bovine serum (FBS) was conventionally incubated in 5% $CO_2$ in an incubator at 37° C. MM.1S-luc cell line was injected with $1.5 \times 10^6$ cells/200 μl PBS via caudal vein (50 mice, half male and half female) for 17 days. Then, all the animals were imaged. The uniformly tumor-bearing mice entered into the experiment group, and were randomly divided into 5 groups (half male, and half female, 8 mice in each group), that is, an extracellular fluid group, a Mock T group, as well as BCMA CART low, medium, and high dose groups. Of those, the extracellular fluid group was injected with extracellular fluid via caudal vein, the Mock T group was injected with Mock T cells via caudal vein, and the BCMA CART low, medium, and high dose groups were injected with BCMA CART cells prepared in Example 4 via caudal vein.

After 3 days, the mice were anesthetized, and intraperitoneally injected with the luciferase substrate. The tumor loading of the control groups (the extracellular fluid group and the Mock T Group), and the BCMA CART treatment groups were observed by the small animal in vivo imaging system. The results on Day 3 and Day 7 after treatment are shown in FIG. 5 and FIG. 6 respectively.

Figure 5:
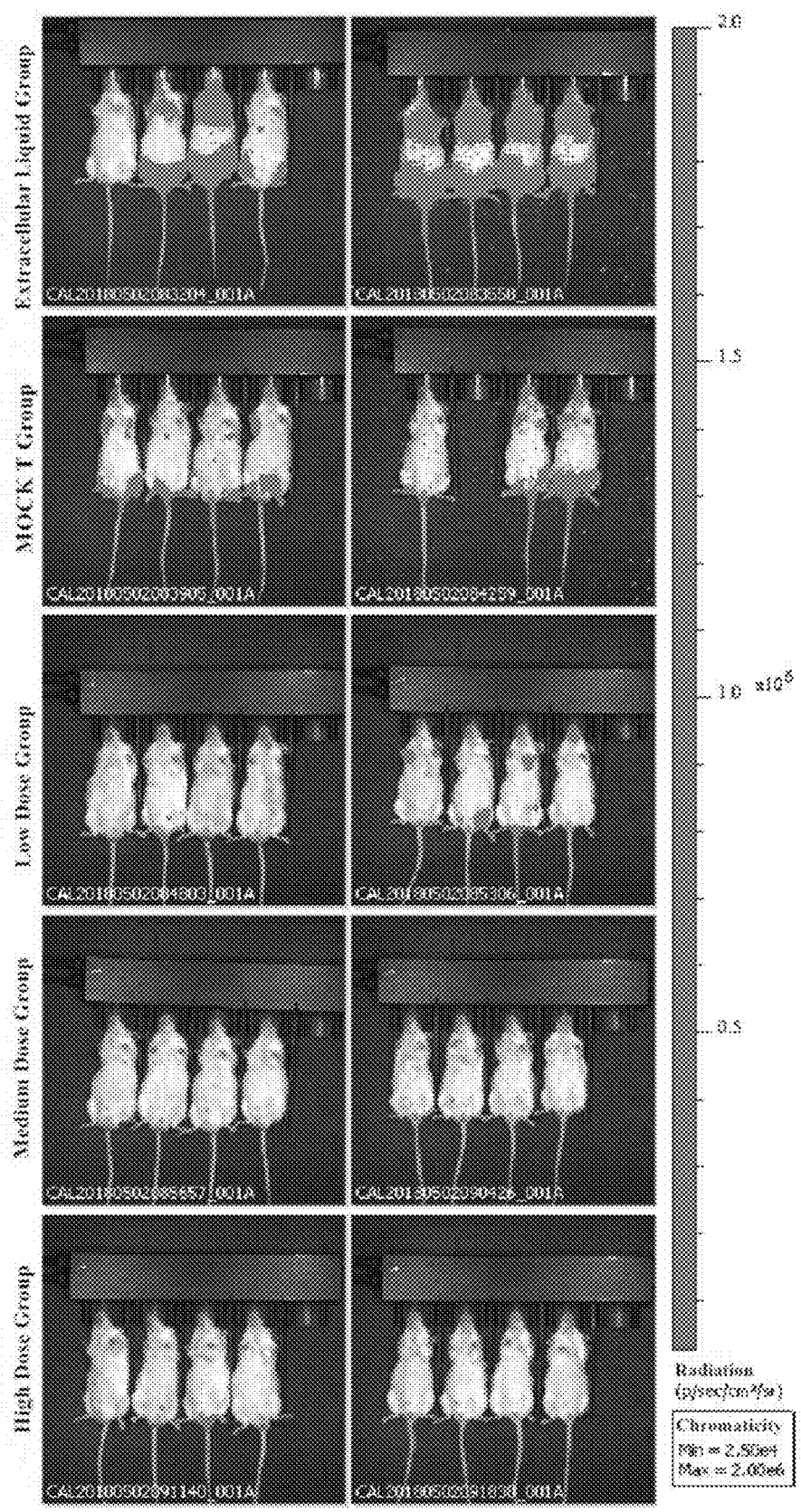
FIG. 5 shows a detection result of the treatment of tumor-bearing mice with the immune cells comprising the chimeric antigen receptor of the present application.
Figure 6:
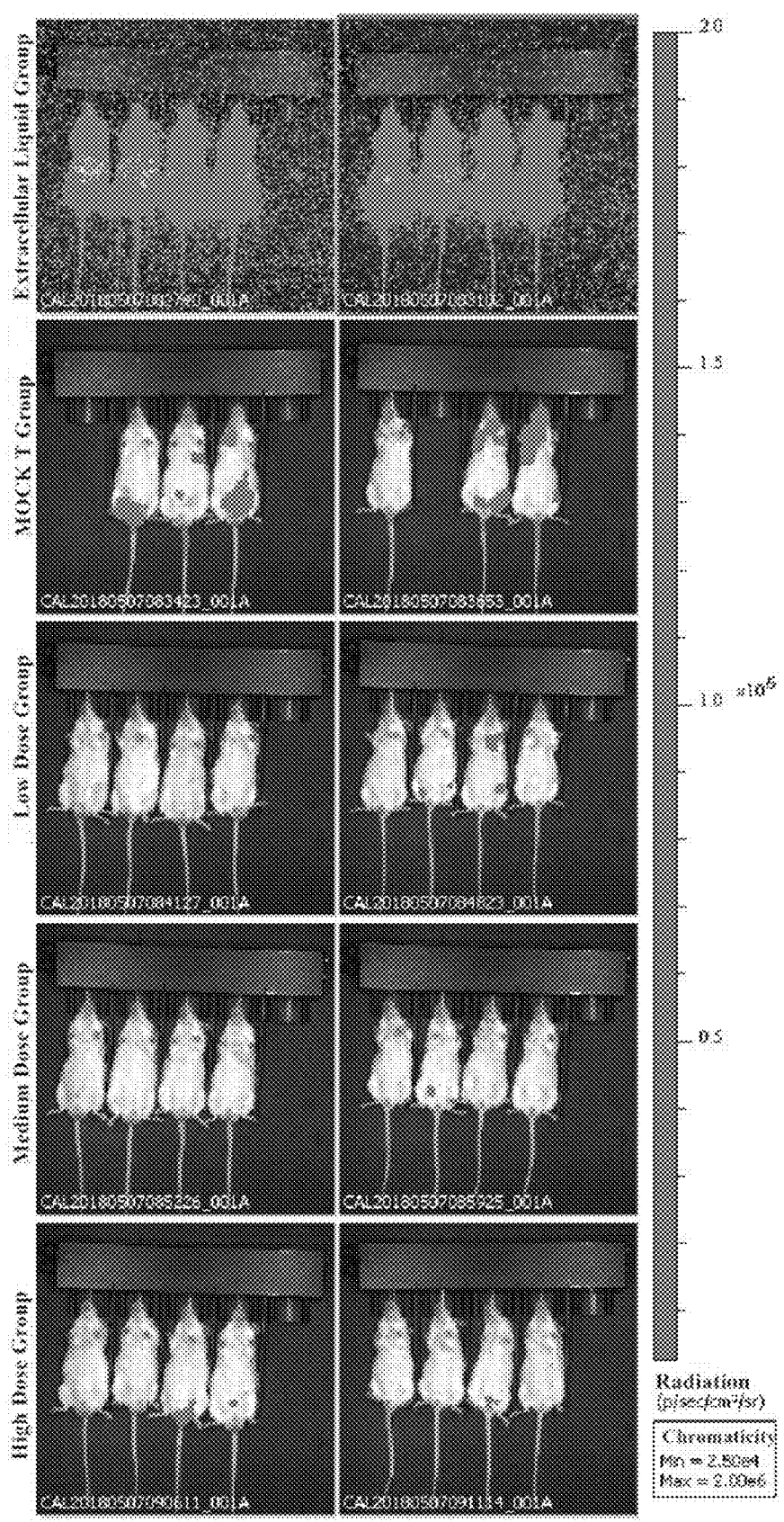
FIG. 6 shows a detection result of the treatment of tumor-bearing mice with the immune cells comprising the chimeric antigen receptor of the present application.

The results in FIG. 5 show that there is almost no tumor cell imaging in the BCMA CART high, and medium-dose treatment groups, while the tumor loading in the control groups is heavy, indicating that BCMA CART can effectively clear the BCMA-positive tumor cells. After BCMA CART cells were infused back into vein, the fluorescence signal intensity in mice on Day 3 began to decrease as compared with the extracellular fluid group and the MOCK T group, indicating that the tumor loading was decreasing. It can be seen from FIG. 6 that the fluorescence signal intensity in mice on Day 7 was substantially undetectable. It can be seen that BCMA CART also shows a strong therapeutic effect on diseases associated with BCMA expression in an animal in vivo experiment.

Until now, those skilled in the art should recognize that although a plurality of exemplary embodiments of the present application have been shown and described in details herein, however, many other variations or modifications in accordance with the principles of the present application can be directly determined or derived from the disclosure of the present application without departing from the spirit or scope of the present application. Thus, the scope of the present application should be understood and considered to encompass all of the other variations or modifications.

The invention claimed is:

1. A chimeric antigen receptor (CAR), comprising:
   a BCMA binding domain;
   a transmembrane domain;
   a co-stimulatory domain; and
   an intracellular signaling domain,
   wherein the BCMA binding domain comprises a heavy chain variable region comprising a heavy chain complementarity determining region 1 (HCDR1), a heavy chain complementarity determining region 2 (HCDR2), and a heavy chain complementarity determining region 3 (HCDR3),
   wherein the amino acid sequence of the HCDR1 is as set forth in SEQ ID NO: 1,
   wherein the amino acid sequence of the HCDR2 is as set forth in SEQ ID NO: 2, and
   wherein the amino acid sequence of the HCDR3 is as set forth in SEQ ID NO: 3.

2. The CAR of claim 1, wherein the BCMA binding domain comprises the amino acid sequence as set forth in SEQ ID NO: 4.

3. The CAR of claim 1, wherein the transmembrane domain comprises a transmembrane domain of one of the following proteins α, β, or ζ chain of a T-cell receptor, CD28, CD3e, CD45, CD4, CD5, CD8a, CD9, CD16, CD22, CD33, CD37, CD64, CD80, CD86, CD134, CD137, and CD154.

4. The CAR of claim 1, wherein the transmembrane domain comprises the amino acid sequence as set forth in SEQ ID NO:5.

5. The CAR of claim 1, wherein the BCMA binding domain is linked to the transmembrane domain via a hinge region.

6. The CAR of claim 5, wherein the hinge region comprises the amino acid sequence as set forth in SEQ ID NO:6.

7. The CAR of claim 1, wherein the co-stimulatory domain is a co-stimulatory domain of CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKG2C, SLP76, TRIM, or ZAP70.

8. The CAR of claim 1, wherein the co-stimulatory domain comprises the amino acid sequence as set forth in SEQ ID NO: 7.

9. The CAR of claim 1, wherein the intracellular signaling domain comprises a signaling domain of CD3ζ.

10. The CAR of claim 1, wherein the intracellular signaling domain comprises the amino acid sequence as set forth in SEQ ID NO:8.

11. The CAR of claim 1, further comprising:
    a leader sequence comprising the amino acid sequence as set forth in SEQ ID NO:9.

12. The CAR of claim 1, comprising the amino acid sequence as set forth in SEQ ID NO:10 or SEQ ID NO:11.

13. The CAR of claim 1, comprising more than one co-stimulatory domain.

14. An immune effector cell, comprising the CAR of claim 1.

15. The cell of claim 14, which is selected from the group consisting of a T lymphocyte cell and a natural killer (NK) cell.

16. A method of treating a disease or disorder associated with an expression of BCMA, the method comprising:
    administering a therapeutically effective amount of the cell of claim 15 to a subject in need thereof.

17. The method of claim 16, wherein the disease or disorder associated with the expression of BCMA is cancer or malignant tumor.

18. The method of claim 16, wherein the disease or disorder associated with the expression of BCMA is selected from the group consisting of B cell acute lymphoblastic leukemia, T cell acute lymphoblastic leukemia, acute lymphoblastic leukemia, chronic myeloid leukemia, chronic lymphocytic leukemia, B cell prolymphocytic leukemia, blast cell plasmacytoid dendritic cytoma, Burkitt's lymphoma, diffuse large B cell lymphoma, follicular lymphoma, hairy cell leukemia, small cell follicular lymphoma, large cell follicular lymphoma, malignant lymphoproliferative condition, MALT lymphoma, mantle cell lymphoma, marginal zone lymphoma, multiple myeloma, myelodysplasia, and myelodysplastic syndrome, non-Hodgkin lymphoma, plasmablast lymphoma, plasmacytoid dendritic cytoma, Waldenstrom macroglobulinemia, prostatic cancer, pancreatic cancer, lung cancer, myeloma, MGUS, plasmacytoma, systemic amyloid light chain amyloidosis, and POEMS syndrome.

* * * * *

SEQUENCE LISTING

```
<160> NUMBER OF SEQ ID NOS: 16

<210> SEQ ID NO 1
<211> LENGTH: 5
<212> TYPE: PRT
<213> ORGANISM: Artificial Sequence
<220> FEATURE:
<223> OTHER INFORMATION: amino acid sequence of HCDR1 of BCMA binding
      domain

<400> SEQUENCE: 1

Thr Tyr Phe Met Ala
1               5

<210> SEQ ID NO 2
<211> LENGTH: 18
<212> TYPE: PRT
<213> ORGANISM: Artificial Sequence
<220> FEATURE:
<223> OTHER INFORMATION: amino acid sequence of HCDR2 of BCMA binding
      domain

<400> SEQUENCE: 2

Gly Gly Ile Arg Trp Ser Asp Gly Val Pro His Tyr Ala Asp Ser Val
1               5                   10                  15

Lys Gly

<210> SEQ ID NO 3
<211> LENGTH: 14
```

```
<212> TYPE: PRT
<213> ORGANISM: Artificial Sequence
<220> FEATURE:
<223> OTHER INFORMATION: amino acid sequence of HCDR3 of BCMA binding
      domain

<400> SEQUENCE: 3

Cys Ala Ser Arg Gly Ile Ala Asp Gly Ser Asp Phe Gly Ser
1               5                   10

<210> SEQ ID NO 4
<211> LENGTH: 120
<212> TYPE: PRT
<213> ORGANISM: Artificial Sequence
<220> FEATURE:
<223> OTHER INFORMATION: amino acid sequence of BCMA binding domain

<400> SEQUENCE: 4

Glu Val Gln Leu Gln Ala Ser Gly Gly Gly Leu Ala Gln Pro Gly Gly
1               5                   10                  15

Ser Leu Arg Leu Ser Cys Ala Ala Ser Gly Arg Thr Phe Ser Thr Tyr
            20                  25                  30

Phe Met Ala Trp Phe Arg Gln Pro Pro Gly Lys Gly Leu Glu Tyr Val
        35                  40                  45

Gly Gly Ile Arg Trp Ser Asp Gly Val Pro His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Phe Cys
                85                  90                  95

Ala Ser Arg Gly Ile Ala Asp Gly Ser Asp Phe Gly Ser Tyr Gly Gln
            100                 105                 110

Gly Thr Gln Val Thr Val Ser Ser
        115                 120

<210> SEQ ID NO 5
<211> LENGTH: 21
<212> TYPE: PRT
<213> ORGANISM: Artificial Sequence
<220> FEATURE:
<223> OTHER INFORMATION: amino acid sequence of transmembrane domain

<400> SEQUENCE: 5

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 6
<211> LENGTH: 49
<212> TYPE: PRT
<213> ORGANISM: Artificial Sequence
<220> FEATURE:
<223> OTHER INFORMATION: amino acid sequence of hinge region

<400> SEQUENCE: 6

Pro Ala Lys Pro Thr Thr Thr Pro Ala Pro Arg Pro Pro Thr Pro Ala
1               5                   10                  15

Pro Thr Ile Ala Ser Gln Pro Leu Ser Leu Arg Pro Glu Ala Cys Arg
            20                  25                  30

Pro Ala Ala Gly Gly Ala Val His Thr Arg Gly Leu Asp Phe Ala Cys
        35                  40                  45
```

Asp

<210> SEQ ID NO 7
<211> LENGTH: 42
<212> TYPE: PRT
<213> ORGANISM: Artificial Sequence
<220> FEATURE:
<223> OTHER INFORMATION: amino acid sequence of co-stimulatory domain

<400> SEQUENCE: 7

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 8
<211> LENGTH: 114
<212> TYPE: PRT
<213> ORGANISM: Artificial Sequence
<220> FEATURE:
<223> OTHER INFORMATION: amino acid sequence of intracellular signaling
      domain

<400> SEQUENCE: 8

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Gln Arg Arg Lys Asn Pro Gln Glu Gly Leu Tyr Asn Glu Leu
    50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg

<210> SEQ ID NO 9
<211> LENGTH: 21
<212> TYPE: PRT
<213> ORGANISM: Artificial Sequence
<220> FEATURE:
<223> OTHER INFORMATION: amino acid sequence of leader sequence

<400> SEQUENCE: 9

Met Ala Leu Pro Val Thr Ala Leu Leu Leu Pro Leu Ala Leu Leu Leu
1               5                   10                  15

His Ala Ala Arg Pro
            20

<210> SEQ ID NO 10
<211> LENGTH: 369
<212> TYPE: PRT
<213> ORGANISM: Artificial Sequence
<220> FEATURE:
<223> OTHER INFORMATION: amino acid sequence of a complete CARincluding a leader sequence

<400> SEQUENCE: 10

| | | | | | | | | | | | | | | | |
|---|---|---|---|---|---|---|---|---|---|---|---|---|---|---|---|
| Met | Ala | Leu | Pro | Val | Thr | Ala | Leu | Leu | Leu | Pro | Leu | Ala | Leu | Leu | Leu |
| 1 | | | | 5 | | | | | 10 | | | | | 15 | |
| His | Ala | Ala | Arg | Pro | Glu | Val | Gln | Leu | Gln | Ala | Ser | Gly | Gly | Gly | Leu |
| | | | 20 | | | | | 25 | | | | | 30 | | |
| Ala | Gln | Pro | Gly | Gly | Ser | Leu | Arg | Leu | Ser | Cys | Ala | Ala | Ser | Gly | Arg |
| | | | 35 | | | | 40 | | | | | 45 | | | |
| Thr | Phe | Ser | Thr | Tyr | Phe | Met | Ala | Trp | Phe | Arg | Gln | Pro | Pro | Gly | Lys |
| | | 50 | | | | 55 | | | | 60 | | | | | |
| Gly | Leu | Glu | Tyr | Val | Gly | Gly | Ile | Arg | Trp | Ser | Asp | Gly | Val | Pro | His |
| 65 | | | | 70 | | | | | 75 | | | | | 80 | |
| Tyr | Ala | Asp | Ser | Val | Lys | Gly | Arg | Phe | Thr | Ile | Ser | Arg | Asp | Asn | Ala |
| | | | 85 | | | | | 90 | | | | | 95 | | |
| Lys | Asn | Thr | Val | Tyr | Leu | Gln | Met | Asn | Ser | Leu | Arg | Ala | Glu | Asp | Thr |
| | | | 100 | | | | | 105 | | | | | 110 | | |
| Ala | Val | Tyr | Phe | Cys | Ala | Ser | Arg | Gly | Ile | Ala | Asp | Gly | Ser | Asp | Phe |
| | | | 115 | | | | 120 | | | | | 125 | | | |
| Gly | Ser | Tyr | Gly | Gln | Gly | Thr | Gln | Val | Thr | Val | Ser | Ser | Pro | Ala | Lys |
| | | | 130 | | | | 135 | | | | | 140 | | | |
| Pro | Thr | Thr | Thr | Pro | Ala | Pro | Arg | Pro | Pro | Thr | Pro | Ala | Pro | Thr | Ile |
| 145 | | | | 150 | | | | | 155 | | | | | 160 | |
| Ala | Ser | Gln | Pro | Leu | Ser | Leu | Arg | Pro | Glu | Ala | Cys | Arg | Pro | Ala | Ala |
| | | | 165 | | | | | 170 | | | | | 175 | | |
| Gly | Gly | Ala | Val | His | Thr | Arg | Gly | Leu | Asp | Phe | Ala | Cys | Asp | Ile | Tyr |
| | | | 180 | | | | | 185 | | | | | 190 | | |
| Ile | Trp | Ala | Pro | Leu | Ala | Gly | Thr | Cys | Gly | Val | Leu | Leu | Leu | Ser | Leu |
| | | | 195 | | | | | 200 | | | | | 205 | | |
| Val | Ile | Thr | Leu | Tyr | Cys | Lys | Arg | Gly | Arg | Lys | Lys | Leu | Leu | Tyr | Ile |
| | | 210 | | | | 215 | | | | | 220 | | | | |
| Phe | Lys | Gln | Pro | Phe | Met | Arg | Pro | Val | Gln | Thr | Thr | Gln | Glu | Glu | Asp |
| 225 | | | | 230 | | | | | 235 | | | | | 240 | |
| Gly | Cys | Ser | Cys | Arg | Phe | Pro | Glu | Glu | Glu | Glu | Gly | Gly | Cys | Glu | Leu |
| | | | 245 | | | | | 250 | | | | | 255 | | |
| Arg | Val | Lys | Phe | Ser | Arg | Ser | Ala | Asp | Ala | Pro | Ala | Tyr | Gln | Gln | Gly |
| | | | 260 | | | | | 265 | | | | | 270 | | |
| Gln | Asn | Gln | Leu | Tyr | Asn | Glu | Leu | Asn | Leu | Gly | Arg | Arg | Glu | Glu | Tyr |
| | | | 275 | | | | | 280 | | | | | 285 | | |
| Asp | Val | Leu | Asp | Lys | Arg | Arg | Gly | Arg | Asp | Pro | Glu | Met | Gly | Gly | Lys |
| | | | 290 | | | | | 295 | | | | | 300 | | |
| Pro | Gln | Arg | Arg | Lys | Asn | Pro | Gln | Glu | Gly | Leu | Tyr | Asn | Glu | Leu | Gln |
| 305 | | | | 310 | | | | | 315 | | | | | 320 | |
| Lys | Asp | Lys | Met | Ala | Glu | Ala | Tyr | Ser | Glu | Ile | Gly | Met | Lys | Gly | Glu |
| | | | 325 | | | | | 330 | | | | | 335 | | |
| Arg | Arg | Arg | Gly | Lys | Gly | His | Asp | Gly | Leu | Tyr | Gln | Gly | Leu | Ser | Thr |
| | | | 340 | | | | | 345 | | | | | 350 | | |
| Ala | Thr | Lys | Asp | Thr | Tyr | Asp | Ala | Leu | His | Met | Gln | Ala | Leu | Pro | Pro |
| | | | 355 | | | | | 360 | | | | | 365 | | |
| Arg | | | | | | | | | | | | | | | |

<210> SEQ ID NO 11
<211> LENGTH: 348
<212> TYPE: PRT

<213> ORGANISM: Artificial Sequence
<220> FEATURE:
<223> OTHER INFORMATION: amino acid sequence of a complete CARnot including a leader sequence

<400> SEQUENCE: 11

```
Glu Val Gln Leu Gln Ala Ser Gly Gly Gly Leu Ala Gln Pro Gly Gly
1               5                   10                  15

Ser Leu Arg Leu Ser Cys Ala Ala Ser Gly Arg Thr Phe Ser Thr Tyr
            20                  25                  30

Phe Met Ala Trp Phe Arg Gln Pro Pro Gly Lys Gly Leu Glu Tyr Val
        35                  40                  45

Gly Gly Ile Arg Trp Ser Asp Gly Val Pro His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Phe Cys
                85                  90                  95

Ala Ser Arg Gly Ile Ala Asp Gly Ser Asp Phe Gly Ser Tyr Gly Gln
            100                 105                 110

Gly Thr Gln Val Thr Val Ser Ser Pro Ala Lys Pro Thr Thr Thr Pro
        115                 120                 125

Ala Pro Arg Pro Pro Thr Pro Ala Pro Thr Ile Ala Ser Gln Pro Leu
    130                 135                 140

Ser Leu Arg Pro Glu Ala Cys Arg Pro Ala Ala Gly Gly Ala Val His
145                 150                 155                 160

Thr Arg Gly Leu Asp Phe Ala Cys Asp Ile Tyr Ile Trp Ala Pro Leu
                165                 170                 175

Ala Gly Thr Cys Gly Val Leu Leu Leu Ser Leu Val Ile Thr Leu Tyr
            180                 185                 190

Cys Lys Arg Gly Arg Lys Lys Leu Leu Tyr Ile Phe Lys Gln Pro Phe
        195                 200                 205

Met Arg Pro Val Gln Thr Thr Gln Glu Glu Asp Gly Cys Ser Cys Arg
    210                 215                 220

Phe Pro Glu Glu Glu Glu Gly Gly Cys Glu Leu Arg Val Lys Phe Ser
225                 230                 235                 240

Arg Ser Ala Asp Ala Pro Ala Tyr Gln Gln Gly Gln Asn Gln Leu Tyr
                245                 250                 255

Asn Glu Leu Asn Leu Gly Arg Arg Glu Glu Tyr Asp Val Leu Asp Lys
            260                 265                 270

Arg Arg Gly Arg Asp Pro Glu Met Gly Gly Lys Pro Gln Arg Arg Lys
        275                 280                 285

Asn Pro Gln Glu Gly Leu Tyr Asn Glu Leu Gln Lys Asp Lys Met Ala
    290                 295                 300

Glu Ala Tyr Ser Glu Ile Gly Met Lys Gly Glu Arg Arg Arg Gly Lys
305                 310                 315                 320

Gly His Asp Gly Leu Tyr Gln Gly Leu Ser Thr Ala Thr Lys Asp Thr
                325                 330                 335

Tyr Asp Ala Leu His Met Gln Ala Leu Pro Pro Arg
            340                 345
```

<210> SEQ ID NO 12
<211> LENGTH: 1110
<212> TYPE: DNA
<213> ORGANISM: Artificial Sequence
<220> FEATURE:

<223> OTHER INFORMATION: nucleic sequence encoding CARincluding a leader
      sequence

<400> SEQUENCE: 12

| | | | | | |
|---|---|---|---|---|---|
| atggccttac | cagtgaccgc | cttgctcctg | ccgctggcct | tgctgctcca | cgccgccagg | 60 |
| ccggaagtcc | aactccaggc | ttccggtggc | ggtctggcac | agcctggagg | gtccctgcgg | 120 |
| ctctcctgcg | cagcaagtgg | caggactttc | agtacctact | ttatggcctg | gttcagacag | 180 |
| ccacctggca | aaggcctcga | atacgtcgga | gggattaggt | ggtctgacgg | tgtccctcac | 240 |
| tacgctgaca | gtgtgaaggg | tcggttcacc | attagcagag | acaacgctaa | gaatacagtg | 300 |
| tacctgcaaa | tgaactcact | gagagctgag | gatactgctg | tgtacttctg | cgcatctcgc | 360 |
| ggaatcgctg | acgggtcaga | ctttggctcc | tatggacagg | gcacccaggt | gactgtgagt | 420 |
| tccccagcga | agcccaccac | gacgccagcg | ccgcgaccac | caacaccggc | gccaccatc  | 480 |
| gcgtcgcagc | ccctgtccct | gcgcccagag | gcgtgccggc | cagcggcggg | gggcgcagtg | 540 |
| cacacgaggg | ggctggactt | cgcctgtgat | atctacatct | gggcgccctt | ggccgggact | 600 |
| tgtgggtcc  | ttctcctgtc | actggttatc | acccttact  | gcaaacgggg | cagaaagaaa | 660 |
| ctcctgtata | tattcaaaca | accatttatg | agaccagtac | aaactactca | agaggaagat | 720 |
| ggctgtagct | gccgatttcc | agaagaagaa | gaaggaggat | gtgaactgag | agtgaagttc | 780 |
| agcaggagcg | cagacgcccc | cgcgtaccag | cagggccaga | accagctcta | taacgagctc | 840 |
| aatctaggac | aagagagga  | gtacgatgtt | ttggacaaga | cgtggccg   | ggaccctgag | 900 |
| atggggggaa | agccgcagag | aaggaagaac | cctcaggaag | gcctgtacaa | tgaactgcag | 960 |
| aaagataaga | tggcggaggc | ctacagtgag | attgggatga | aaggcgagcg | ccggagggc  | 1020 |
| aagggcacg  | atggccttta | ccagggtctc | agtacagcca | ccaaggacac | ctacgacgcc | 1080 |
| cttcacatgc | aggccctgcc | ccctcgctaa | | | | 1110 |

<210> SEQ ID NO 13
<211> LENGTH: 1047
<212> TYPE: DNA
<213> ORGANISM: Artificial Sequence
<220> FEATURE:
<223> OTHER INFORMATION: nucleic sequence encoding CARnot including a
      leader sequence

<400> SEQUENCE: 13

| | | | | | |
|---|---|---|---|---|---|
| gaagtccaac | tccaggcttc | cggtggcggt | ctggcacagc | ctggagggtc | cctgcggctc | 60 |
| tcctgcgcag | caagtggcag | gactttcagt | acctactta  | tggcctggtt | cagacagcca | 120 |
| cctggcaaag | gcctcgaata | cgtcggaggg | attaggtggt | ctgacggtgt | ccctcactac | 180 |
| gctgacagtg | tgaagggtcg | gttcaccatt | agcagagaca | acgctaagaa | tacagtgtac | 240 |
| ctgcaaatga | actcactgag | agctgaggat | actgctgtgt | acttctgcgc | atctcgcgga | 300 |
| atcgctgacg | ggtcagactt | tggctcctat | ggacagggca | cccaggtgac | tgtgagttcc | 360 |
| ccagcgaagc | ccaccacgac | gccagcgccg | cgaccaccaa | caccggcgcc | accatcgcg  | 420 |
| tcgcagcccc | tgtccctgcg | cccagaggcg | tgccggccag | cggcggggg  | cgcagtgcac | 480 |
| acgaggggc  | tggacttcgc | ctgtgatatc | tacatctggg | cgcccttggc | cgggacttgt | 540 |
| ggggtccttc | tcctgtcact | ggttatcacc | ctttactgca | aacggggcag | aaagaaactc | 600 |
| ctgtatatat | tcaaacaacc | atttatgaga | ccagtacaaa | ctactcaaga | ggaagatggc | 660 |
| tgtagctgcc | gatttccaga | agaagaagaa | ggaggatgtg | aactgagagt | gaagttcagc | 720 |
| aggagcgcag | acgccccgc  | gtaccagcag | ggccagaacc | agctctataa | cgagctcaat | 780 |

```
ctaggacgaa gagaggagta cgatgttttg gacaagagac gtggccggga ccctgagatg    840
gggggaaagc cgcagagaag gaagaaccct caggaaggcc tgtacaatga actgcagaaa    900
gataagatgg cggaggccta cagtgagatt gggatgaaag gcgagcgccg gaggggcaag    960
gggcacgatg gcctttacca gggtctcagt acagccacca aggacaccta cgacgccctt   1020
cacatgcagg ccctgccccc tcgctaa                                        1047

<210> SEQ ID NO 14
<211> LENGTH: 553
<212> TYPE: DNA
<213> ORGANISM: Artificial Sequence
<220> FEATURE:
<223> OTHER INFORMATION: nucleic sequence of EF1 promoter

<400> SEQUENCE: 14
aaggatctgc gatcgctccg gtgcccgtca gtgggcagag cgcacatcgc ccacagtccc     60
cgagaagttg gggggagggg tcggcaattg aacgggtgcc tagagaaggt ggcgcggggt    120
aaactgggaa agtgatgtcg tgtactggct ccgcctttttt cccgagggtg ggggagaacc   180
gtatataagt gcagtagtcg ccgtgaacgt tctttttcgc aacgggtttg ccgccagaac    240
acagctgaag cttcgagggg ctcgcatctc tccttcacgc gcccgccgcc ctacctgagg    300
ccgccatcca cgccggttga gtcgcgttct gccgcctccc gctgtggtg cctcctgaac     360 tgcgtccgcc gtctaggtaa gtttaaagct caggtcgaga ccgggccttt gtccggcgct    420
cccttggagc ctacctagac tcagccggct ctccacgctt tgcctgaccc tgcttgctca    480
actctacgtc tttgtttcgt tttctgttct gcgccgttac agatccaagc tgtgaccggc    540
gcctacgcta gac                                                       553

<210> SEQ ID NO 15
<211> LENGTH: 423
<212> TYPE: DNA
<213> ORGANISM: Artificial Sequence
<220> FEATURE:
<223> OTHER INFORMATION: nucleic sequence of BCMA sdAb I

<400> SEQUENCE: 15
atggccttac cagtgaccgc cttgctcctg ccgctggcct tgctgctcca cgccgccagg     60
ccggaagtcc aactccaggc ttccggtggc ggtctggcac agcctggagg gtccctgcgg    120
ctctcctgcg cagcaagtgg caggactttc agtacctact ttatggcctg gttcagacag    180
ccacctggca aaggcctcga atacgtcgga gggattaggg gtctgacggt gtccctcac     240 tacgctgaca gtgtgaaggg tcggttcacc attagcagag acaacgctaa gaatacagtg    300
tacctgcaaa tgaactcact gagagctgag gatactgctg tgtacttctg cgcatctcgc    360
ggaatcgctg acgggtcaga ctttggctcc tatggacagg gcacccaggt gactgtgagt    420
tcc                                                                  423

<210> SEQ ID NO 16
<211> LENGTH: 687
<212> TYPE: DNA
<213> ORGANISM: Artificial Sequence
<220> FEATURE:
<223> OTHER INFORMATION: second generation CAR structure gene

<400> SEQUENCE: 16
ccagcgaagc ccaccacgac gccagcgccg cgaccaccaa caccggcgcc caccatcgcg     60
```

-continued

```
tcgcagcccc tgtccctgcg cccagaggcg tgccggccag cggcgggggg cgcagtgcac    120 acgaggggc tggacttcgc ctgtgatatc tacatctggg cgcccttggc cgggacttgt    180
ggggtccttc tcctgtcact ggttatcacc ctttactgca aacggggcag aaagaaactc    240
ctgtatatat tcaaacaacc atttatgaga ccagtacaaa ctactcaaga ggaagatggc    300
tgtagctgcc gatttccaga agaagaagaa ggaggatgtg aactgagagt gaagttcagc    360
aggagcgcag acgccccgc gtaccagcag ggccagaacc agctctataa cgagctcaat    420
ctaggacgaa gagaggagta cgatgttttg gacaagagac gtggccggga ccctgagatg    480
gggggaaagc cgcagagaag gaagaaccct caggaaggcc tgtacaatga actgcagaaa    540
gataagatgg cggaggccta cagtgagatt gggatgaaag gcgagcgccg gaggggcaag    600
gggcacgatg gcctttacca gggtctcagt acagccacca aggacaccta cgacgccctt    660
cacatgcagg ccctgccccc tcgctaa                                        687
```